(12) United States Patent
Shimizu et al.

(10) Patent No.: US 8,936,859 B2
(45) Date of Patent: Jan. 20, 2015

(54) CYCLOPHOSPHAZENE COMPOUND, LUBRICANT COMPRISING SAME, AND MAGNETIC DISK

(75) Inventors: Tsuyoshi Shimizu, Kobe (JP); Nagayoshi Kobayashi, Kobe (JP)

(73) Assignee: Moresco Corporation, Hyogo (JP)

(*) Notice: Subject to any disclaimer, the term of this patent is extended or adjusted under 35 U.S.C. 154(b) by 128 days.

(21) Appl. No.: 13/641,508

(22) PCT Filed: Apr. 20, 2011

(86) PCT No.: PCT/JP2011/060493
§ 371 (c)(1),
(2), (4) Date: Oct. 16, 2012

(87) PCT Pub. No.: WO2011/136379
PCT Pub. Date: Nov. 3, 2011

(65) Prior Publication Data
US 2013/0034749 A1    Feb. 7, 2013

(30) Foreign Application Priority Data
Apr. 26, 2010    (JP) .................... 2010-101122

(51) Int. Cl.
*G11B 5/66* (2006.01)
*G11B 5/725* (2006.01)
(Continued)

(52) U.S. Cl.
CPC ............ *G11B 5/725* (2013.01); *C07F 9/65815* (2013.01); *C08G 65/007* (2013.01);
(Continued)

(58) Field of Classification Search
CPC ................. C07F 9/65815; C10M 2217/003; C10M 2225/003
USPC ........................... 428/835.8; 508/422; 564/13
See application file for complete search history.

(56) References Cited

U.S. PATENT DOCUMENTS 6,080,486 A * 6/2000 Falcone et al. ............... 428/421
6,730,403 B1 5/2004 Shirai et al.
(Continued)

FOREIGN PATENT DOCUMENTS

EP    2 157 117    2/2010
JP    2000-260017    9/2000
(Continued)

OTHER PUBLICATIONS

International Search Report issued Jun. 21, 2011 in International (PCT) Application No. PCT/JP2011/060493, of which the present application is the national stage.
(Continued)

*Primary Examiner* — Holly Rickman
(74) *Attorney, Agent, or Firm* — Wenderoth, Lind & Ponack, L.L.P.

(57) ABSTRACT

A cyclophosphazene compound of the formula (I), and lubricants and magnetic disks using the compound (I)

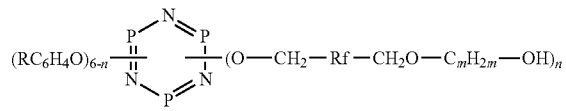

wherein n is 2, 3 or 4, m is an integer of 1 to 12, R is $C_{1-4}$ fluoroalkyl and Rf is $-CF_2O(CF_2CF_2O)_x(CF_2O)_yCF_2-$ or $-CF_2CF_2O(CF_2CF_2CF_2O)_zCF_2CF_2-$ in which x, y and z are each 0 or a positive real number to give a number average molecular weight of 500 to 4000 to a fluoropolyether of the formula $HOCH_2-Rf-CH_2OH$ including said Rf, the fluoropolyether having a molecular weight distribution (PD) of 1.0 to 1.5.

9 Claims, 1 Drawing Sheet

(51) Int. Cl.
  *C07F 9/6593* (2006.01)
  *C08G 65/00* (2006.01)
  *C10M 105/74* (2006.01)

(52) U.S. Cl.
  CPC ......... *C10M105/74* (2013.01); *C10M 2213/04* (2013.01); *C10M 2223/08* (2013.01); *C10N 2220/021* (2013.01); *C10N 2230/06* (2013.01); *C10N 2240/204* (2013.01); *C10N 2250/121* (2013.01); *C10N 2250/141* (2013.01)
  USPC ........... 428/835.8; 564/13; 428/422; 428/582

(56) References Cited

U.S. PATENT DOCUMENTS 7,510,999 B2 * 3/2009 Deng et al. .................... 508/422
8,679,656 B2 * 3/2014 Kobayashi et al. ........ 428/835.8

2008/0020171 A1   1/2008 Wakabayashi et al.
2009/0291325 A1 * 11/2009 Xu et al. ...................... 428/800
2011/0143165 A1   6/2011 Kobayashi et al.
2012/0251843 A1 * 10/2012 Yan et al. ..................... 428/800

FOREIGN PATENT DOCUMENTS

| JP | 2002-275484 | 9/2002 |
| JP | 2004-352999 | 12/2004 |
| JP | 2010-108583 | 5/2010 |
| WO | 2006/009057 | 1/2006 |
| WO | 2010/027096 | 3/2010 |

OTHER PUBLICATIONS

Supplementary European Search Report issued Dec. 14, 2012 in European Patent Application No. 11775160.

* cited by examiner

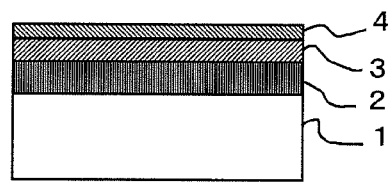

CYCLOPHOSPHAZENE COMPOUND, LUBRICANT COMPRISING SAME, AND MAGNETIC DISK

TECHNICAL FIELD

The present invention relates to a cyclophosphazene compound having a cyclophosphazene group and hydroxyl groups in the molecule and lubricants and magnetic disks using the compound.

BACKGROUND ART

With an increase in the recording density of magnetic disks, the distance between the magnetic disk serving as a recording medium and the head for use in recording of information or playback has become almost nil close to contact therebetween. The magnetic disk is provided over the surface thereof with a carbon protective film or lubricant film for the purpose of diminishing abrasion due to the contact or sliding of the head thereon or preventing contamination of the disk surface.

The carbon protective film is produced generally by the sputtering process or CVD process. Since the disk surface is protected with the two films, i.e., the carbon protective film and the lubricant film thereover, the interaction between the carbon protective film and the lubricant is important.

The lubricants generally in use are perfluoropolyethers having functional groups. Examples of functional groups are hydroxyl, amino and cyclophosphazene group. More specific examples of lubricants include PHOSFAROL A20H, product of Matsumura Oil Research Corporation which is represented by the formula (II)

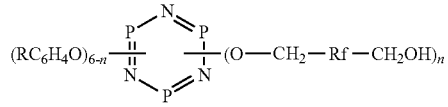

wherein n is 3 and Rf is —$CF_2CF_2O(CF_2CF_2CF_2O)_z$ $CF_2CF_2$— (Patent Literature 1).

Particularly, lubricants having a phosphazene group are materials having high resistance to decomposition and known as materials for giving high durability to magnetic disks (for example, Patent Literature 2, 3). However, with reference to the lubricant of Patent Literature 2, claim 1 therein defines a compound wherein n is an integer of 1 to 5, whereas the preparation process of the patent concerned affords only a mixture which is not satisfactory in lubricating performance. With the lubricant of Patent Literature 3, a cyclophosphazene ring has a fluoropolyether main chain wherein the number of substituent is 1, and the lubricant is low in bonded ratio as listed in Table 1 given later.

Patent Literature 1: WO 2010/027096
Patent Literature 2: JP 2000-260017A
Patent Literature 3: JP 2004-352999A

SUMMARY OF THE INVENTION

Under the condition wherein the head is at such a distance from the disk that it is almost in contact therewith, the use of the lubricant having a phosphazene group and highly resistant to decomposition involves the problem that the head needs to be prevented from moving into contact with the disk. Heretofore proposed as means for dissolving this problem are techniques for causing the lubricant to adsorb to the carbon protective film more effectively by introducing plural of perfluoropolyethers into cyclophosphazene group and incorporating hydroxyl group at the terminal of the group (for example, Patent Literature 1). However, the lubricant of Patent Literature 1 cannot form strong bonding with a polar site of the carbon protective film under the lubricant, due to steric influence of fluorine atom adjacent to hydroxyl group, possibly spattering the lubricant at high-speed rotation of the disk.

Further, it is effective to adjust a molecular weight distribution (PD, weight average molecular weight/number average molecular weight) of fluoropolyether of phosphazene compound in order to improve lubricant property and adherence to the protective layer.

An object of the present invention is to provide a stable compound which remains free of decomposition even when brought into contact with the head and which exhibits good adhering properties to the carbon protective film, and lubricants and magnetic disks using the compound.

DISCLOSURE OF THE INVENTION

The present invention provides the following.
1. A cyclophosphazene compound of the formula (I)

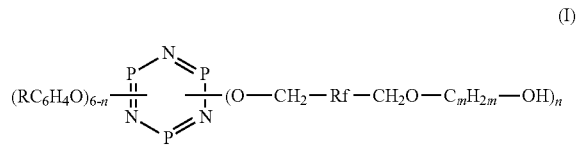

wherein n is 2, 3 or 4, m is an integer of 1 to 12, R is $C_{1-4}$ fluoroalkyl and Rf is —$CF_2O(CF_2CF_2O)_x(CF_2O)_yCF_2$— or —$CF_2CF_2O(CF_2CF_2CF_2O)_zCF_2CF_2$— in which x, y and z are each 0 or a positive real number to give a number average molecular weight of 500 to 4000 to a fluoropolyether of the formula $HOCH_2$—Rf—$CH_2OH$ including said Rf, the fluoropolyether having a molecular weight distribution (PD) of 1.0 to 1.5.

2. A lubricant containing a compound of the formula (I).
3. A magnetic disk comprising a substrate having at least a recording layer and a protective layer formed thereover and a lubricating layer provided over the resulting surface, the lubricating layer containing a compound of the formula (I).

The present perfluoropolyether compound having cyclophosphazene group in the molecular main chain and alkylalcohol group in the molecular terminal provides a lubricant which solves the two problems of excellent adhering properties and resistance to lubricant decomposition at the same time.

EMBODIMENT OF PRACTICING THE INVENTION

Process for Preparing Lubricant

The lubricant of the invention is obtained, for example, by reacting a straight-chain fluoropolyether having hydroxyl at one of opposite terminals and an alkylacetal group, alkylester group or alkylsilyl group at the other terminal with a cyclophosphazene halide compound substituted with phenoxy group, and thereafter hydrolyzing the resulting compound. Stated more specifically, the lubricant is prepared by the process to be described below.

(a) Preparation of Straight-Chain Fluoropolyether Having Hydroxyl at One Terminal and an Alkylacetal Group, Alkylester Group or Alkylsilyl Group at the Other Terminal A straight-chain fluoropolyether having hydroxyl at opposite terminals is mixed with a compound reactive with hydroxyl to produce an alkylacetal group, alkylester group or alkylsilyl group, and sodium metal, and the mixture is stirred with heating. The reaction temperature is 20 to 90° C., preferably 50 to 70° C. The reaction time is 20 to 200 hours, preferably 110 to 130 hours. The compound for forming an alkylacetal group, alkylester group or alkylsilyl group is used preferably in an amount of 0.5 to 2.0 equivalents relative to the perfluoropolyether. Sodium metal is used preferably in an amount of 0.5 to 4.0 equivalents relative to the perfluoropolyether. The reaction mixture is thereafter purified, for example, by column chromatography to obtain a straight-chain fluoropolyether having hydroxyl at one terminal and an alkylacetal group, alkylester group or alkylsilyl group at the other terminal.

The fluoropolyether having hydroxyl at opposite terminals can be, for example, a compound of the formula $HOCH_2-Rf-CH_2OH$ wherein Rf is $-CF_2O(CF_2CF_2O)_x(CF_2O)_yCF_2-$ or $-CF_2CF_2O(CF_2CF_2CF_2O)_zCF_2CF_2-$. The fluoropolyether is 500 to 4000, preferably 1000 to 3000, more preferably 1800 to 2200, in number average molecular weight. The number average molecular weight mentioned is a value measured by $^{19}$F-NMR using JNM-ECX400, product of JEOL Ltd. For NMR measurement, the sample itself was used without dilution with a solvent. As a reference for chemical shift, a known peak was used which is a portion of fluoropolyether skeleton structure.

x is a real number of 1 to 33, preferably 1 to 25, more preferably 1 to 18. y is a real number of 0 to 60, preferably 0 to 43 and more preferably 0 to 31. z is a real number of 1 to 23, preferably 4 to 17, more preferably 9 to 12.

The fluoropolyether of the foregoing formula $HOCH_2-Rf-CH_2OH$ is a compound having a molecular weight distribution. The molecular weight distribution (PD), which is weight average molecular weight/number average molecular weight, is 1.0 to 1.5, preferably 1.0 to 1.4, more preferably 1.0 to 1.3 and particularly preferably 1.05 to 1.2. The molecular weight distribution is a characteristic value obtained by using HPLC-8220GPC, product of Tosoh Co., Ltd., column (PLgel Mixed E), product of Polymer Laboratories, eluent which is HCFC-type alternative CFC and a non-functional perfluoropolyether serving as a reference material.

Examples of compounds reactive with hydroxyl for forming an alkylacetal group, alkylester group or alkylsilyl group are an ether compound of the formula

$YC_mH_{2m}OCH_2OR^a$ (Y is halogen atom, m is an integer of 1 to 12, $R^a$ is $C_{1-10}$ alkyl, pyrryl, $C_{6-10}$ aryl or $C_{6-10}$ aralkyl), ester compound of the formula

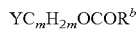

$YC_mH_{2m}OCOR^b$ (Y is halogen atom, m is an integer of 1 to 12, $R^b$ is $C_{1-10}$ alkyl, $C_{6-10}$ aryl or $C_{6-10}$ aralkyl) and silane compound of the formula

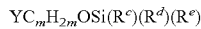

$YC_mH_{2m}OSi(R^c)(R^d)(R^e)$ (Y is halogen atom, m is an integer of 1 to 12, $R^c$, $R^d$ and $R^e$ are same or different and are each $C_{1-10}$ alkyl, $C_{6-10}$ aryl or $C_{6-10}$ aralkyl).

Examples of $C_{1-10}$ alkyl groups are methyl, ethyl, propyl, butyl, hexyl and octyl.

Examples of $C_{6-10}$ aryl groups are phenyl, tolyl and isopropylphenyl.

Examples of $C_{6-10}$ aralkyl groups are benzyl, phenylethyl, tolylmethyl and isopropylphenylethyl.

Specific examples are 2-chloroethyl methoxymethyl ether, 2-bromoethyl methoxymethyl ether, 2-chloroethyl ethoxymethyl ether, 2-bromoethyl ethoxymethyl ether, 2-(2-chloroethoxy)tetrahydro-2H-pyrran, 2-(2-bromoethoxy)tetrahydro-2H-pyrran, 2-chloroethyl benzyloxymethyl ether, 2-bromoethyl benzyloxymethyl ether, 2-chloroethyl acetate, 2-bromoethyl acetate, 2-chloroethyl benzoate, 2-bromoethyl benzoate, 2-chloroethyl trimethylsilyl ether, 2-bromoethyl trimethylsilyl ether, 2-chloroethyl triisopropylsilyl ether, 2-bromoethyl triisopropylsilyl ether, 2-chloroethyl t-butyldimethylsilyl ether, 2-bromoethyl t-butyldimethylsilyl ether, 4-chlorobutyl methoxymethyl ether, 4-bromobutyl methoxymethyl ether, 4-chlorobutyl ethoxymethyl ether, 4-bromobutyl ethoxymethyl ether, 2-(4-chlorobutoxy)tetrahydro-2H-pyrran, 2-(4-bromobutoxy)tetrahydro-2H-pyrran, 4-chlorobutyl benzyloxymethyl ether, 4-bromobutyl benzyloxymethyl ether, 4-chlorobutyl acetate, 4-bromobutyl acetate, 4-chlorobutyl benzoate, 4-bromobutyl benzoate, 4-chlorobutyl trimethylsilyl ether, 4-bromobutyl trimethylsilyl ether, 4-chlorobutyl triisopropylsilyl ether, 4-bromobutyl triisopropylsilyl ether, 4-chlorobutyl t-butyldimethylsilyl ether, 4-bromobutyl t-butyldimethylsilyl ether, 6-chlorohexyl methoxymethyl ether, 4-bromohexyl methoxymethyl ether, 6-chlorohexyl ethoxymethyl ether, 6-bromohexyl ethoxymethyl ether, 2-(6-chlorohexyloxy)tetrahydro-2H-pyrran, 2-(6-bromohexyloxy)tetrahydro-2H-pyrran, 6-chlorohexyl benzyloxymethyl ether, 6-bromohexyl benzyloxymethyl ether, 6-chlorohexyl acetate, 6-bromohexyl acetate, 6-chlorohexyl benzoate, 6-bromohexyl benzoate, 6-chlorohexyl trimethylsilyl ether, 6-bromohexyl trimethylsilyl ether, 6-chlorohexyl triisopropylsilyl ether, 6-bromohexyl triisopropylsilyl ether, 6-chlorohexyl t-butyldimethylsilyl ether, 6-bromohexyl t-butyldimethylsilyl ether, 8-chlorooctyl methoxymethyl ether, 8-bromooctyl methoxymethyl ether, 8-chlorooctyl ethoxymethyl ether, 8-bromooctyl ethoxymethyl ether, 2-(8-chlorooctyloxy)tetrahydro-2H-pyrran, 2-(8-bromooctyloxy)tetrahydro-2H-pyrran, 8-chlorooctyl benzyloxymethyl ether, 8-bromooctyl benzyloxymethyl ether, 8-chlorooctyl acetate, 8-bromooctyl acetate, 8-chlorooctyl benzoate, 8-bromooctyl benzoate, 8-chlorooctyl trimethylsilyl ether, 8-bromooctyl trimethylsilyl ether, 8-chlorooctyl triisopropylsilyl ether, 8-bromooctyl triisopropylsilyl ether, 8-chlorooctyl t-butyldimethylsilyl ether, 8-bromooctyl t-butyldimethylsilyl ether, 12-chlorododecyl methoxymethyl ether, 12-bromododecyl methoxymethyl ether, 12-chlorododecyl ethoxymethyl ether, 12-bromododecyl ethoxymethyl ether, 2-(12-chlorododecyloxy)tetrahydro-2H-pyrran, 2-(12-bromododecyoxy)tetrahydro-2H-pyrran, 12-chlorododecyl benzyloxymethyl ether, 12-bromododecyl benzyloxymethyl ether, 12-chlorododecyl acetate, 12-bromododecyl acetate, 12-chlorododecyl benzoate, 12-bromododecyl benzoate, 12-chlorododecyl trimethylsilyl ether, 12-bromododecyl trimethylsilyl ether, 12-chlorododecyl triisopropylsilyl ether, 12-bromododecyl triisopropylsilyl ether, 12-chlorododecyl t-butyldimethylsilyl ether and 12-bromododecyl t-butyldimethylsilyl ether.

(b) Preparation of Lubricant of the Invention

The fluoropolyether obtained by the above procedure (a) and a cyclophosphazene of the formula $(RC_6H_4O)_{6-n}-(P_3N_3)-X_n$ having n halogen atoms are stirred with heating along with sodium or like alkali metal. n is 2, 3 or 4, and the cyclophosphazene material is at least 80%, preferably at least 90%, in purity. The reaction temperature is 30 to 100° C., preferably 50 to 80° C. The reaction time is 20 to 100 hours, preferably 50 to 80 hours. It is desirable to use 0.5 to 3.0 equivalents of the perfluoropolyether obtained by the foregoing procedure (a) and 0.5 to 3.0 equivalents of the alkali metal relative to the halogen atoms. The reaction may be conducted in a solvent, followed, for example, by dewatering. The acetal group, ester group or silyl group remaining at one terminal of the perfluoropolyether is thereafter removed as by hydrolysis for deprotection (removal of the acetal group, ester group or silyl group), followed by fractionation by column chromatography, supercritical fluid extraction or the like to obtain the desired compound as a single fraction.

R in the substituent of the cyclophosphazene of the formula $(RC_6H_4O)_{6-n}$—$(P_3N_3)$—$X_n$ is a fluoroalkyl group having 1 to 4 carbon atoms, such as perfluoroalkyl, 1,1,2,2-tetrafluoroethyl, 1,1,2,2,3,3-hexafluoropropyl and 1,1,2,2,3,3,4,4-octafluorobutyl having 1 to 4 carbon atoms. The position of the substitution with R may be any of the ortho, meta and para positions.

In the cyclophosphazene of the formula $(RC_6H_4O)_{6-n}$—$(P_3N_3)$—$X_n$ having n halogen atoms, X can be, for example, chlorine, bromine or iodine.

When the lubricant of the present invention is to be used for magnetic disks, n is preferably 2, 3 or 4, more preferably 3 or 4, and most preferably 3, m is preferably 1 to 12, more preferably 2 to 6, and most preferably 2 to 4.

The compound of the present invention is applied to the magnetic disk surface by diluting the compound with a solvent and coating the disk surface with the diluted compound. Examples of useful solvents are PF-5060, PF-5080, HFE-7100, HFE-7200 and HFE-7300 manufactured by 3M, Vertrel-XF, product of DuPont, etc. The concentration of the compound as diluted is up to 1 wt. %, preferably 0.001 to 0.1 wt. %.

While the compound of the invention is usable singly, the compound can be used also as mixed in a desired ratio with another material, such as Fomblin Zdol, Ztetraol, Zdol TX, AM manufactured by Solvay Solexis, Demnum manufactured by Daikin Industries, Ltd., Krytox manufactured by DuPont, or the like.

The compound of the present invention enables the head to be spaced by a small distance from the magnetic disk inside magnetic disk devices and is useful as a lubricant for giving improved durability under a sliding condition. The compound of the invention is characterized by the interaction of the hydroxyl at the terminal of the molecule with the polar site present in the carbon protective film and by the interaction of the aromatic group in the molecular chain with carbon unsaturated bonds present in the carbon protective film. Accordingly, the compound is usable as a surface protective film for magnetic heads, photomagnetic recording devices, magnetic tapes, plastics and like organic materials having a carbon protective film, and also as a surface protective film for inorganic materials such as $Si_3N_4$, SiC and $SiO_2$.

FIG. 1 shows a sectional view schematically showing the magnetic disk of the invention. The magnetic disk of the invention comprises a substrate 1, at least one recording layer 2 formed on the substrate 1, a protective layer 3 on the recording layer 2 and a lubricant layer 4 formed thereon, as an outermost layer, which contains the lubricant of the invention. The substrate is composed of aluminum alloy, glass and like ceramics, polycarbonate or the like.

The recording layer of the magnetic disk, i.e., the magnetic layer is composed of mainly elements capable of forming ferromagnetic bodies, such as iron, cobalt or nickel, alloy or oxide containing chromium, platinum or tantalum in addition to such elements. These materials are applied by, e.g., a plating method or a sputtering method. The protective layer is formed of carbon, SiC, $SiO_2$ or the like. The layer is formed by a sputtering method or CVD method.

Lubricant layers presently available are up to 30 Å in thickness, so that when a lubricant having a viscosity of higher than about 100 mPa·s at 20° C. is applied as it is, the resulting film is likely to have an excessively large thickness. Accordingly the lubricant for use in coating is used as dissolved in a solvent. When the compound of the present invention is applied as dissolved in a solvent, the film thickness to be obtained is easy to control in the case where the present compound serves singly as a lubricant and also in the case where the compound is used as mixed with other lubricant. The concentration varies with the method and conditions of application, mixing ratio, etc. The lubricant film of the present invention is preferably 5 to 15 Å in thickness.

In order to assure the lubricant of improved adhesion to the ground layer, the lubricant applied can be subjected to heat treatment or ultraviolet treatment. The heat treatment is conducted at 60 to 150° C., preferably at 80 to 150° C. The ultraviolet treatment is conducted using ultraviolet rays of 185 nm and 254 nm in main wavelength.

The magnetic disk of the invention can be applied to a magnetic disk apparatus which can accommodate the disk and which is provided with a magnetic disk drive including a head for recording, reproducing and erasing information and a motor for rotating the disk; and with a control system for controlling the drive. Examples of recording methods of magnetic disk devices are in-plane magnetic recording, perpendicular magnetic recording and heat-assisted magnetic recording. The lubricant is applicable also to discrete-track magnetic disks and bit-patterned magnetic disks.

BRIEF DESCRIPTION OF THE DRAWING

FIG. 1 is a section view showing the structure of the magnetic disk of the invention. Indicated at 1 is a substrate; at 2, a recording layer; at 3, a protective layer; and at 4, a lubricant layer.

BEST MODE FOR CARRYING OUT THE INVENTION

The invention will be described in more detail with reference to the following examples and test examples to which, however, the invention is not limited.

Example 1

Preparation of (m-$CF_3$—$C_6H_4O)_3$—$(P_3N_3)$—(O—$CH_2$—Rf—$CH_2OCH_2CH_2OH)_3$ (Lubricant 1)

Rf is 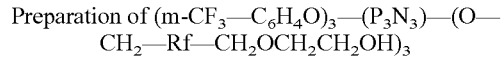.

Ditrifluoromethylbenzene (180 g), 90 g of a fluoropolyether (1995 in number average molecular weight, 1.09 in molecular weight distribution) of the formula $HOCH_2$—$CF_2O(CF_2CF_2O)_x(CF_2O)_yCF_2CH_2$—OH, 2-(2-bromoethoxy)tetrahydro-2H-pyran (18 g) and metallic sodium (4 g) were stirred in an argon atmosphere at 60° C. for 120 hours. The reaction mixture was thereafter washed with water, dewatered and purified by silica gel column chromatography to obtain 30 g of a perfluoropolyether (average molecular weight 2000) having one hydroxyl group at one terminal and a 2-(ethoxy)tetrahydro-2H-pyran group at the other terminal. The compound (30 g) was dissolved in ditrifluoromethylbenzene (60 g), metallic sodium (0.5 g) and 8 g of cyclophosphazene of the formula $(m\text{-}CF_3\text{—}C_6H_4O)_3\text{—}(P_3N_3)\text{—}Cl_3$ having 3 chlorine atoms were added to the solution, and the mixture was stirred at 70° C. for 70 hours. The acetal group was then hydrolyzed at room temperature with p-toluenesulfonic acid (20 g), thereafter washed with water, dewatered and purified by silica gel column chromatography to obtain 12 g of the desired Lubricant 1.

Lubricant 1 was a colorless transparent liquid and 1.75 g/cm³ in density at 20° C. Lubricant 1 was identified by NMR with the result shown.

$^{19}$F-NMR (solvent: none, reference material: $OCF_2C\underline{F}_2C\underline{F}_2CF_2O$ in the obtained product being taken as −125.8 ppm):
δ=−52.1, −53.7, −55.4 ppm
[56 F, —$OC\underline{F}_2O$—],
δ=−64.1 ppm
[9F $(C\underline{F}_3C_6H_4O)_3$—$P_3N_3$—$(OCH_2CF_2\text{—})_3$],
δ=−78.0 ppm, −80.0 ppm
[6F, —$C\underline{F}_2CH_2OCH_2CH_2H$],
δ=−78.7 ppm, −80.7 ppm
[6F $(CF_3C_6H_4O)_3$—$P_3N_3$—$(OCH_2C\underline{F}_2\text{—})_3$],
δ=−89.1 ppm, −90.7 ppm
[118F, —$OC\underline{F}_2C\underline{F}_2O$—]
x=9.8 y=9.4
$^1$H-NMR (solvent: none, reference material: $D_2O$):
δ=3.53~3.82 ppm
[24H, —$CF_2C\underline{H}_2OC\underline{H}_2C\underline{H}_2OH$, $(CF_3C_6H_4O)_3$—$P_3N_3$—$(OC\underline{H}_2CF_2\text{—})_3$],
δ=4.61 ppm
[3H, —$CF_2CH_2OCH_2CH_2O\underline{H}$],
δ=6.78~7.35 ppm
[12H, $(CF_3C_6\underline{H}_4O)_3$—$P_3N_3$—$(OCH_2CF_2\text{—})_3$]

Example 2

Preparation of $(m\text{-}CF_3\text{—}C_6H_4O)_3\text{—}(P_3N_3)\text{—}(O\text{—}CH_2\text{—}Rf\text{—}CH_2OCH_2CH_2OH)_3$ (Lubricant 2)
Rf is —$CF_2CF_2O(CF_2CF_2CF_2O)_zCF_2CF_2$—.

The procedure of Example 1 was repeated with the exception of using a fluoropolyether (1836 in number average molecular weight, 1.17 in molecular weight distribution) of the formula $HOCH_2$—$CF_2CF_2O(CF_2CF_2CF_2O)_zCF_2CF_2CH_2$—OH, whereby 10 g of the desired Lubricant 2 was obtained.

Lubricant 2 was a colorless transparent liquid and had a density of 1.79 g/cm³ at 20° C. Lubricant 2 was identified by NMR with the result shown.

$^{19}$F-NMR (solvent: none, reference material: $OCF_2C\underline{F}_2CF_2O$ in the obtained product being taken as −129.7 ppm):
δ=−83.7 ppm
[118F, —$C\underline{F}_2CF_2C\underline{F}_2O$—],
δ=−86.3 ppm
[6F, $(CF_3C_6H_4O)_3$—$P_3N_3$—$(OCH_2CF_2C\underline{F}_2\text{—})_3$],
δ=−86.7 ppm
[6F, —$C\underline{F}_2CF_2CH_2OCH_2OCH_2CH_2OH$],
δ=−124.4 ppm
[6F, —$CF_2C\underline{F}_2CH_2OCH_2OCH_2CH_2OH$],
δ=−124.8 ppm
[6F, $(CF_3C_6H_4O)_3$—$P_3N_3$—$(OCH_2C\underline{F}_2CF_2\text{—})_3$],
δ=−129.7 ppm
[59F, —$CF_2C\underline{F}_2CF_2O$—],
Z=9.8
$^1$H-NMR (solvent: none, reference material: $D_2O$):
δ=3.72~4.19 ppm
[24H, —$CF_2CF_2C\underline{H}_2OC\underline{H}_2C\underline{H}_2OH$, $(CF_3C_6H_4O)_3$—$P_3N_3$—$(OC\underline{H}_2CF_2CF_2\text{—})_3$],
δ=4.34 ppm
[3H, —$CF_2CF_2CH_2OCH_2CH_2O\underline{H}$],
δ=6.83~7.31 ppm
[12H, $(CF_3C_6\underline{H}_4O)_3$—$P_3N_3$—$(OCH_2CF_2CF_2\text{—})_3$]

Example 3

Preparation of $(m\text{-}CF_3\text{—}C_6H_4O)_3\text{—}(P_3N_3)\text{—}(O\text{—}CH_2\text{—}Rf\text{—}CH_2OCH_2CH_2CH_2OH)_3$ (Lubricant 3)
Rf is —$CF_2O(CF_2CF_2O)_x(CF_2O)_yCF_2$—.

The procedure of Example 1 was repeated with the exception of using 2-(4-bromobutoxy)tetrahydro-2H-pyran in place of 2-(2-bromoethoxy)tetrahydro-2H-pyran, whereby 11 g of the desired Lubricant 3 was obtained.

Lubricant 3 was a colorless transparent liquid and had a density of 1.80 g/cm³ at 20° C. Lubricant 3 was identified by NMR with the result shown.

$^{19}$F-NMR (solvent: none, reference material: $OCF_2C\underline{F}_2C\underline{F}_2CF_2O$ in the obtained product being taken as −125.8 ppm):
δ=−52.1, −53.7, −55.4 ppm
[58F, —$OC\underline{F}_2O$—],
δ=−64.1 ppm
[9F, $(C\underline{F}_3C_6H_4O)_3$—$P_3N_3$—$(OCH_2CF_2\text{—})_3$],
δ=−78.0 ppm, −80.0 ppm
[6F, —$C\underline{F}_2CH_2OCH_2CH_2CH_2OH$],
δ=−78.7 ppm, −80.7 ppm
[6F, $(CF_3C_6H_4O)_3$—$P_3N_3$—$(OCH_2C\underline{F}_2\text{—})_3$],
δ=−89.1 ppm, −90.7 ppm
[113F, —$OC\underline{F}_2C\underline{F}_2O$—]
x=9.4 y=9.6
$^1$H-NMR (solvent: none, reference material: $D_2O$):
δ=1.53~2.07 ppm
[12H, —$CF_2CH_2OCH_2C\underline{H}_2CH_2OH$],
δ=3.53~3.82 ppm
[24H, —$CF_2C\underline{H}_2OC\underline{H}_2CH_2CH_2C\underline{H}_2OH$, $(CF_3C_6H_4O)_3$—$P_3N_3$—$(OC\underline{H}_2CF_2\text{—})_3$],
δ=5.04 ppm
[3H, —$CF_2CH_2OCH_2CH_2CH_2O\underline{H}$],
δ=6.78~7.35 ppm
[12H, $(CF_3C_6\underline{H}_4O)_3$—$P_3N_3$—$(OCH_2CF_2\text{—})_3$]

Example 4

Preparation of $(m\text{-}CF_3\text{—}C_6H_4O)_3\text{—}(P_3N_3)\text{—}(O\text{—}CH_2\text{—}Rf\text{—}CH_2OCH_2CH_2CH_2OH)_3$ (Lubricant 4)
Rf is —$CF_2CF_2O(CF_2CF_2CF_2O)_zCF_2CF_2$—.

The procedure of Example 1 was repeated with the exception of using a fluoropolyether (1836 in number average molecular weight, 1.17 in molecular weight distribution) of the formula $HOCH_2$—$CF_2CF_2O(CF_2CF_2CF_2O)_zCF_2CF_2CH_2$—OH, and using 2-(4-bromobutoxy)-tetrahydro-2H-pyran in place of 2-(2-bromoethoxy)tetrahydro-2H-pyran, whereby 9 g of the desired Lubricant 4 was obtained.

Lubricant 4 was a colorless transparent liquid and had a density of 1.82 g/cm³ at 20° C. Lubricant 4 was identified by NMR with the result shown.

$^{19}$F-NMR (solvent: none, reference material: $OCF_2C\underline{F}_2CF_2O$ in the obtained product being taken as −129.7 ppm):
δ=−83.7 ppm
[114F, —$C\underline{F}_2CF_2C\underline{F}_2O$—],
δ=−86.3 ppm
[6F, $(CF_3C_6H_4O)_3$—$P_3N_3$—$(OCH_2CF_2C\underline{F}_2)_3$],
δ=−86.7 ppm

[6F, —C$\underline{F}$$_2$CF$_2$CH$_2$OCH$_2$OCH$_2$CH$_2$CH$_2$CH$_2$OH],
δ=−124.4 ppm
[6F, —CF$_2$C$\underline{F}$$_2$CH$_2$OCH$_2$CH$_2$CH$_2$CH$_2$OH],
δ=−124.8 ppm
[6F, (CF$_3$C$_6$H$_4$O)$_3$—P$_3$N$_3$—(OCH$_2$C$\underline{F}$$_2$CF$_2$—)$_3$],
δ=−129.7 ppm
[57F, —CF$_2$C$\underline{F}$$_2$CF$_2$O—],
Z=9.5
$^1$H-NMR (solvent: none, reference material: D$_2$O):
δ=1.34~1.70 ppm
[12H, —CF$_2$CF$_2$CH$_2$OCH$_2$C$\underline{H}$$_2$C$\underline{H}$$_2$CH$_2$OH],
δ=3.72~4.19 ppm
[24H, —CF$_2$CF$_2$C$\underline{H}$$_2$OC$\underline{H}$$_2$CH$_2$CH$_2$C$\underline{H}$$_2$OH, (CF$_3$C$_6$H$_4$O)$_3$—P$_3$N$_3$—(OC$\underline{H}$$_2$CF$_2$CF$_2$—)$_3$],
δ=4.34 ppm
[3H, —CF$_2$CF$_2$CH$_2$OCH$_2$CH$_2$CH$_2$CH$_2$O$\underline{H}$],
δ=6.83~7.31 ppm
[12H, (CF$_3$C$_6$$\underline{H}$$_4$O)$_3$—P$_3$N$_3$—(OCH$_2$CF$_2$CF$_2$—)$_3$]

Test Example 1

Measurement of Bonded Ratio

Each of Lubricants 1 to 4 prepared in Examples 1 to 4 was dissolved in Vertrel-XF, product of DuPont. The solution was 0.05 wt. % in the concentration of the lubricant. A magnetic disk, 3.5 inches in diameter, was immersed in the solution for 1 minute and then withdrawn at a rate of 2 mm/s. The disk was thereafter held in a constant-temperature chamber at 150° C. for 10 minutes to promote the adhesion of the lubricant to the disk surface. The average film thickness of the compound on the disk was subsequently measured by a Fourier Transform Infrared Spectrometer (FT-IR). This film thickness was taken as f Å. Next, the disk was immersed in Vertrel-XF for 10 minutes, withdrawn at a rate of 10 mm/s and thereafter allowed to stand at room temperature for the evaporation of the solvent. The compound remaining on the disk was thereafter checked by FT-IR for average film thickness. This film thickness was taken as b Å. The bonded ratio generally in use was used as an indicator for showing the strength of adhesion of the film to the disk. The bonded ratio was expressed by the equation given below.

Bonded ratio (%)=100×b/f

Test Example 2

Evaluation of Retention Property of Lubricant on Disk Under High-Speed Rotation

Each of Lubricants 1 to 4 prepared in Examples 1 to 4 was dissolved in Vertrel-XF, product of DuPont. The solution was 0.05 wt. % in the concentration of the lubricant. A magnetic disk, 3.5 inches in diameter, was immersed in the solution for 1 minute and then withdrawn at a rate of 2 mm/s. The average film thickness of the compound on the disk was subsequently measured by FT-IR. This film thickness was taken as h Å. The disk coated with the lubricant was thereafter rotated at high speed of 15000 rpm for two weeks under temperature of 60 to 70° C. and humidity of 60 to 70 RH %. The compound remaining on the disk was thereafter checked by FT-IR for average film thickness. This film thickness was taken as c Å. The lubricant retention ratio was used as an indicator for showing the strength of retention property of the film to the disk. The lubricant retention ratio was expressed by the equation given below.

Lubricant retention ratio (%)=100×c/h

Test Example 3

Measurement of Decomposition Resistance to Aluminum Oxide

A sample was used for evaluation which was prepared from each of Lubricants 1 to 4, by adding 20 wt. % of Al$_2$O$_3$ to the lubricant, intensely shaking the mixture and thereafter thoroughly agitating the mixture with ultrasonic waves. The sample was checked for decomposition resistance using a thermal analyzer (TG/TDA). The sample was heated at 250° C. for 100 minutes, and the weight reduction of the lubricant was measured. The test was conducted with use of 20 mg of the sample under nitrogen atmosphere. For comparison, 20 mg of each of Lubricants 1 to 4 was thermally analyzed in the same manner as above with the exception of adding no Al$_2$O$_3$.

For comparison, Lubricant 5 and Lubricant 6 of the formula (II) below wherein n is 1 and n is 3, respectively, were used. Also used was Lubricant 7 of the formula HOCH$_2$CH(OH)CH$_2$O—Rf—OCH$_2$CH(OH)—CH$_2$OH having two hydroxyl groups at both terminals respectively.

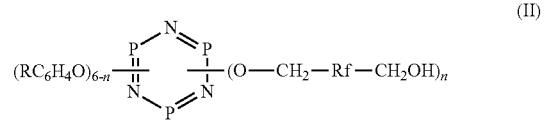

(II)

In the Lubricant 5, R is m-CF$_3$, Rf is —CF$_2$O(CF$_2$CF$_2$O)$_x$(CF$_2$O)$_y$—CF$_2$—, x is 9.1 and y is 8.9. The compound is 1.05 in molecular weight distribution. In the Lubricant 6, R is m-CF$_3$, Rf is —CF$_2$O(CF$_2$CF$_2$O)$_x$(CF$_2$O)$_y$—CF$_2$—, x is 9.4 and y is 9.1. The compound is 1.18 in molecular weight distribution. In the Lubricant 7, Rf is —CF$_2$O(CF$_2$CF$_2$O)$_x$(CF$_2$O)$_y$CF$_2$—, x is 9.8 and y is 9.7. The compound is 1.20 in molecular weight distribution.

Table 1 shows the results of Test Examples 1 to 3. These results indicate that the lubricants 1 to 4 of the invention are confirmed to bond to the magnetic disk at strong adhering properties compared with lubricants 5 to 7. The lubricants 1 to 4 of the invention are confirmed to have higher retention ratio compared with lubricants 5 to 6, and have similar retention ratio to lubricant 7. As to the decomposition resistance to aluminum oxide, the lubricants 1 to 4 of the invention having cyclophosphazene group in the molecule as well as lubricants 5 to 6 have excellent resistance to decomposition. From the above, it is confirmed that the present perfluoropolyether lubricant having cyclophosphazene group and alkylalcohol group in the molecule solves the two problems of resistance to lubricant decomposition and high adhering properties at the same time.

TABLE 1

| Specimen | Bonded ratio(%) | Lubricant retention ratio on disk under high-speed rotation (%) |
| --- | --- | --- |
| Lubricant 1 (Example 1) | 92 | 72 |
| Lubricant 2 (Example 2) | 91 | 71 |
| Lubricant 3 (Example 3) | 95 | 78 |
| Lubricant 4 (Example 4) | 94 | 77 |

TABLE 1-continued

| | | |
|---|---|---|
| Lubricant 5 (Com. Example) | 15 | 23 |
| Lubricant 6 (Com. Example) | 65 | 50 |
| Lubricant 7 (Com. Example) | 40 | 71 |

| Specimen | Ratio of decrease in weight (wt %) with $Al_2O_3$ | Ratio of decrease in weight (wt %) without $Al_2O_3$ |
|---|---|---|
| Lubricant 1 (Example 1) | <1 | <1 |
| Lubricant 2 (Example 2) | <1 | <1 |
| Lubricant 3 (Example 3) | <1 | <1 |
| Lubricant 4 (Example 4) | <1 | <1 |
| Lubricant 5 (Com. Example) | 5 | 6 |
| Lubricant 6 (Com. Example) | <1 | <1 |
| Lubricant 7 (Com. Example) | 39 | 26 |

Example 5

Preparation of Magnetic Disk

Each of Lubricants 1 to 4 was dissolved in Vertrel-XF, product of DuPont. The solution was 0.05 wt. % in the concentration of the compound. A magnetic disk, 3.5 inches in diameter, was immersed in the solution for 1 minute and then withdrawn at a rate of 2 mm/s. The disk was thereafter dried at 150° C. for 10 minutes. The coated compound was thereafter checked by FT-IR for film thickness.

Table 2 shows the results. It was confirmed that the magnetic disk can be obtained which is coated with the present compound and solves the two problems of high adhering properties and resistance to decomposition at the same time.

TABLE 2

| Specimen | Film thickness (Å) |
|---|---|
| Lubricant 1 | 14 |
| Lubricant 2 | 13 |
| Lubricant 3 | 15 |
| Lubricant 4 | 14 |

INDUSTRIAL APPLICABILITY

The present perfluoropolyether compound having cyclophosphazene group in the molecular main chain and alkylalcohol group in the molecular terminal provides a lubricant which solves the two problems of excellent adhering properties and resistance to lubricant decomposition at the same time.

The invention claimed is:

1. A compound represented by formula (I):

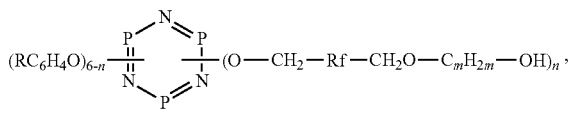

(I)

wherein n is 2, 3 or 4, m is 2, R is $C_{1-4}$ fluoroalkyl and Rf is —$CF_2O(CF_2CF_2O)_x(CF_2O)_yCF_2$— or —$CF_2CF_2O(CF_2CF_2CF_2O)_zCF_2CF_2$— in which x, y and z are each 0 or a positive real number to give a number average molecular weight of 500 to 4000 to a fluoropolyether of the formula $HOCH_2$—Rf—$CH_2OH$ including said Rf, the fluoropolyether having a molecular weight distribution (PD) of 1.0 to 1.5.

2. The compound as defined in claim 1, wherein n is 3 or 4, and x, y and z are each 0 or a positive real number to give the above number average molecular weight of 1000 to 3000.

3. The compound as defined in claim 1, wherein n is 3, and x, y and z are each 0 or a positive real number to give the above number average molecular weight of 1800 to 2200.

4. A lubricant containing a compound of formula (I):

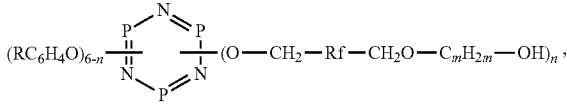

(I)

wherein n is 2, 3 or 4, m is 2, R is $C_{1-4}$ fluoroalkyl and Rf is —$CF_2O(CF_2CF_2O)_x(CF_2O)_yCF_2$— or —$CF_2CF_2O(CF_2CF_2CF_2O)_zCF_2CF_2$— in which x, y and z are each 0 or a positive real number to give a number average molecular weight of 500 to 4000 to a fluoropolyether of the formula $HOCH_2$—Rf—$CH_2OH$ including said Rf, the fluoropolyether having a molecular weight distribution (PD) of 1.0 to 1.5.

5. The lubricant as defined in claim 4, wherein n is 3 or 4, and x, y and z are each 0 or a positive real number to give the above number average molecular weight of 1000 to 3000.

6. The lubricant as defined in claim 4, wherein n is 3, and x, y and z are each 0 or a positive real number to give the above number average molecular weight of 1800 to 2200.

7. A magnetic disk comprising a substrate having at least a recording layer and a protective layer formed thereover and a lubricating layer provided over the resulting surface, the lubricating layer containing a compound of formula (I):

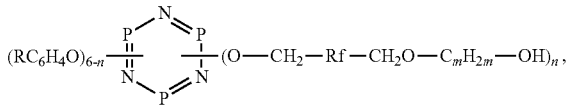

(I)

wherein n is 2, 3 or 4, m is 2, R is $C_{1-4}$ fluoroalkyl and Rf is —$CF_2O(CF_2CF_2O)_x(CF_2O)_yCF_2$— or —$CF_2CF_2O(CF_2CF_2CF_2O)_zCF_2CF_2$— in which x, y and z are each 0 or a positive real number to give a number average molecular weight of 500 to 4000 to a fluoropolyether of the formula $HOCH_2$—Rf—$CH_2OH$ including said Rf, the fluoropolyether having a molecular weight distribution (PD) of 1.0 to 1.5.

8. The magnetic disk as defined in claim 7, wherein n is 3 or 4, and x, y and z are each 0 or a positive real number to give the above number average molecular weight of 1000 to 3000.

9. The magnetic disk as defined in claim 7, wherein n is 3, and z are each 0 or a positive real number to give the above number average molecular weight of 1800 to 2200.

* * * * *